(12) United States Patent
Herring (10) Patent No.: US 8,485,034 B2
(45) Date of Patent: Jul. 16, 2013

(54) ACOUSTIC CONFOCAL INTERFEROMETRY MICROSCOPE

(76) Inventor: Rodney Arthur Herring, Victoria (CA)

( * ) Notice: Subject to any disclaimer, the term of this patent is extended or adjusted under 35 U.S.C. 154(b) by 679 days.

(21) Appl. No.: 12/636,780

(22) Filed: Dec. 14, 2009

(65) Prior Publication Data

US 2011/0141481 A1  Jun. 16, 2011

(51) Int. Cl.
*G01N 29/06* (2006.01)
(52) U.S. Cl.
USPC .......................................................... 73/606
(58) Field of Classification Search
USPC ............................................................. 73/606
See application file for complete search history.

(56) References Cited

U.S. PATENT DOCUMENTS

| | | | | |
|---|---|---|---|---|
| 3,911,729 A * | 10/1975 | Collins | ............................ | 73/603 |
| 4,209,856 A * | 6/1980 | Henning et al. | ................. | 367/87 |
| 5,383,457 A * | 1/1995 | Cohen | ............................ | 600/443 |
| 7,639,365 B2 * | 12/2009 | Herring | ............................ | 356/458 |
| 2003/0053373 A1 * | 3/2003 | Erikson | ............................ | 367/88 |
| 2004/0024314 A1 * | 2/2004 | Lee et al. | ........................ | 600/437 |

* cited by examiner

*Primary Examiner* — Peter Macchiarolo
*Assistant Examiner* — Rose M Miller (57) ABSTRACT

A Confocal Interferometry microscope for use with a suitably selected acoustic emitter and acoustic detector for providing three-dimensional information on the state of an object is presented. The microscope has a coherent wavelength source for producing a coherent beam, scanning means for moving said coherent beam in a suitably selected pattern, and means for producing and focusing an object beam and an interference beam to an object focal point and an interference focal point, respectively. The object beam has a transmission path of essentially the same length of the transmission path of the interference beam. The object beam intercepts an object at the object focal point while the interference beam passes by the object. There are also means for defining the object beam and the interference beam based on the position of the object focal point and the geometry of the convergence angles and means for producing an interference pattern between the object focal point and the interference focal point.

18 Claims, 6 Drawing Sheets

ACOUSTIC CONFOCAL INTERFEROMETRY MICROSCOPE

FIELD OF THE INVENTION

The present invention relates to an Acoustic Confocal Interferometry microscope. Additionally, this invention relates to acoustic confocal interferometry.

BACKGROUND OF THE INVENTION

The use of beams of radiation to obtain information about an object by detecting the amplitude or phase of the beam is well known for scientific and medical purposes. For example, the phase information of a beam that passes through an object can provide information on the object's temperature, composition, magnetic field or electrostatic field, whereas amplitude measurements can provide information on the opaqueness or density of the object. The beams are comprised of waves of radiation, where a wave can be described as having both an amplitude, A, and phase, $\phi$, described mathematically as, $$\psi = A\exp(\phi i) \qquad 1)$$

The information obtained from the diagnostic method depends on whether it is detecting the amplitude or both the amplitude and phase of a beam's wave. If the diagnostic method measures only a beam's amplitude, as is the case for Ultrasound and X-ray, only density differences in the object are reported. If the diagnostic method can detect both the amplitude and phase, it can, for example, provide information on the object's temperature, composition, elasticity, strain field, magnetic or electrostatic fields. For acoustic radiation, i.e., acoustic beams, the phase of a beam is modified by an object's refractive index, where the refractive index is dependent on the object's temperature and composition and is a measure of the acoustic beam's speed of sound. Hence, use of the above prior art limits the information that can be obtained. An additional disadvantage of a number of diagnostic imaging techniques such as X-ray imaging methods is the strength of radiation employed. Levels employed may have the potential to damage cells in the body.

Examples of an application where the measurement of temperature and/or composition is important include medical diagnostics aimed at understanding the function of organs, tissue and diseased regions in the body. Presently medical researchers do not have good means to non-invasively measure the internal temperature and composition of the body.

Confocal scanning laser microscopes were developed in the 1980s for seeing three-dimensional objects. Confocal scanning laser microscopy uses a laser beam passing through an object to create a three-dimensional amplitude image of the object by detecting the amplitude of the beam through a pinhole aperture placed confocal with a point on a focal plane of the object.

Confocal microscopes have now found widespread applications in the materials, biological, and medical sciences. As a diagnostic tool, confocal microscopes are limited to detecting only thin tissue and the density differences of objects, which produce amplitude differences of the detected beam. They do not measure the object's phase information. Hence, confocal microscopes cannot measure an object's composition or temperature.

Standard interferometry microscopes, standard holography microscopes, and standard holographic interferometry microscopes have been used to measure both the phase and the amplitude of objects, giving important information of objects such as their density, composition and temperature. Interferometry microscopes and holographic interferometry microscopes are different from holography microscopes. Interferometry microscopes and holographic interferometry microscopes make relative measurements of the state of an object such as 3 degrees above room temperature whereas holography microscopes make absolute measurements of the state of an object such as a human body having a temperature of 98.6 degrees Fahrenheit. These microscopes create a three dimensional amplitude image and phase image of the object by measuring both the phase and the amplitude. However, the three-dimensional information measured from these microscopes comes only from the surface of the object and not at points within the object.

The concept of marrying the techniques of confocal microscopy and holography using laser beams is disclosed in U.S. Pat. No. 7,639,365, entitled, "Confocal Scanning Holography Microscope", issued Dec. 29, 2009. The microscopes described in U.S. Pat. No. 7,639,365 measure the absolute phase of the object and cannot be used to image the inside of the human body as laser beams do not readily pass through the human body.

Acoustic microscopes including Ultrasound are now widely used to image the inside of the body such as the fetus in the womb and blood flow in arteries and veins. These microscopes measure the intensity of the acoustic beam reflected off surfaces such as bones and interfaces such as the interface between the embryonic fluid and fetus. These microscopes cannot measure the intensity and phase of the beam passing through or reflected from soft tissue such as muscles or embryonic fluid. These microscopes also cannot measure temperature or composition as they only use the intensity of the acoustic beams and not the phase of the acoustic beams.

Accordingly, it is an object of the present invention to overcome the above deficiencies of the prior art.

SUMMARY OF THE INVENTION

An Acoustic Confocal Interferometry (ACI) microscope for obtaining interferograms from points on the surfaces and inside transparent objects is provided for the three dimensional measurement of the amplitudes and phases of an acoustic beam passing through, or reflected from, an object. The ACI microscope has two pinhole (PH) apertures in the optical system placed confocal to a point in the object. The PH apertures allow an object beam and an interference beam to interfere on an observation plane where an interferogram is formed and recorded. The convergence angle of the beam onto the object and the pinhole aperture position define the three-dimensional volume of the object being measured. Each interferogram is equivalent to an equation, containing the amplitude and phase information of the beam having interacted with the part of the object given by the convergence angle of the beam onto the object and the pinhole aperture. "N" number of interferograms of the object are taken by the ACI microscope and they are used to solve for "N" number of three-dimensional points describing the three-dimensional object From the phase information obtained from the interferograms, the refraction index of the object, n, can be determined, which is defined as the ratio of the speed of sound (that is, the speed of the acoustic beam) in air, cair, to the speed of sound in the object, c, for each point describing the three dimensional object. That is $$n = c_{air}/c \qquad 2)$$

The refractive index of the object can be used to determine the object's state, such as its temperature or composition.

In one embodiment, an Acoustic Confocal Interferometry microscope for use with a suitably selected coherent acoustic or ultrasound source, for the production of an acoustic or ultrasound coherent beam, and a suitably selected detector for providing three dimensional information on an object is provided. The microscope comprises:

an acoustic or ultrasound coherent wavelength source for producing an acoustic or ultrasound coherent beam;

scanning means for moving said coherent beam in a suitably selected pattern;

means for producing an object beam and an interference beam;

object beam focusing means for focusing the object beam to an object focal point;

an interference beam focusing means for focusing the interference beam to an interference beam focal point, wherein the interference beam focusing means is other than the object focusing means;

the object beam focusing means and the interference beam focusing means configured to produce a suitably selected convergence angle, at a suitably selected position said object beam having a transmission path of essentially the same length of a transmission path of said interference beam, said object beam intercepting an object at the object focal point and said interference beam passing by the object;

means for defining the object beam and the interference beam based on the geometry of said convergence angle and said position of said object focal point and said interference focal point; and means for producing an interference pattern between said object focal point and said interference focal point, such that in use, information is collected about the object by a detector.

Preferable, the means for producing said object beam and said interference beam is a splitting means and more preferably the splitting means is a biprism.

It is also preferable that said means for focusing said object beam is comprised of two object beam mirrors and said means for focusing said interference beam is comprised of two interference beam mirrors.

It is also preferable that said means for scanning said object beam and said interference beam through the object is comprised of one or more of:

means to shift said object;

means to shift said microscope; and a combination of means to shift said object beam mirrors and means to shift an object beam pinhole aperture, for defining the object beam and the interference beam.

The means to shift said object is preferably a first or a fourth translation stage.

The means to shift said microscope is preferably a second or a fifth translation stage.

The means to shift each object beam mirror is preferably a rotating scanner.

The means to shift said object beam pinhole aperture is preferably a third or a sixth translation stage.

It is advantageous that a means for defining the object beam and the interference beam based on the geometry of said convergence angle and said position of said object focal point and said interference focal point is confocal with said first object focal point and said first interference focal point.

The means for defining the object beam and the interference beam based on the geometry of said convergence angle and said position of said object focal point and said interference focal point is preferably defined as a dual pinhole aperture for limiting passage of said object and said interference beam therethrough.

Preferably, means for producing an interference pattern between said object focal point and said interference focal point comprises a means for collecting said first object focal point and said first interference focal point after said first object focal point and after said first interference focal point and a means for focusing said collected object and interference beams to a second object focal point and a second interference focal point at the dual pinhole aperture.

The means to shift said object is preferably the fourth-translation stage.

The means to shift said microscope is preferably the fifth translation stage.

The means to shift said object beam pinhole aperture is preferably the sixth translation stage.

A method for providing three dimensional information on an object is also provided. The method comprises projecting an acoustic or ultrasound coherent beam from an acoustic or ultrasound coherent wavelength source, splitting the beam into an object beam and an interference beam, independently focusing the resultant two beams using separate optics, ensuring the length of the two beams are essentially equivalent, intercepting the object with said object beam at an object focal point, avoiding the object with the interference beam while having an interference focal point on the same plane as the object focal point, refocusing the two beams to second focal points that are confocal with the first focal points, limiting the beams and forming an interference pattern for detecting.

The method preferably further comprises intercepting and reflecting said interference beam at said interference beam focal point, and reflecting said object beam off the object before refocusing said beams.

An acoustic confocal interferometry microscope is also provided. It comprises:

a scanner configured to receive and scan an acoustic beam;

an acoustic beam splitter to produce an object beam and an interference beam;

an object beam shaping system configured to focus the object beam to an object focal point;

an interference beam shaping system configured to focus the interference beam to an interference focal point, the systems configured to converge the beams at a selected convergence angle at a selected position, herein the object beam intercepts an object at the object focal point; and an acoustic detection system configured to receive the object beam and the interference beam and produce an interference of the object beam and the interference beam.

BRIEF DESCRIPTION OF THE DRAWINGS

The present invention will be described in conjunction with the drawings in which.

DETAILED DESCRIPTION

Figure 1:
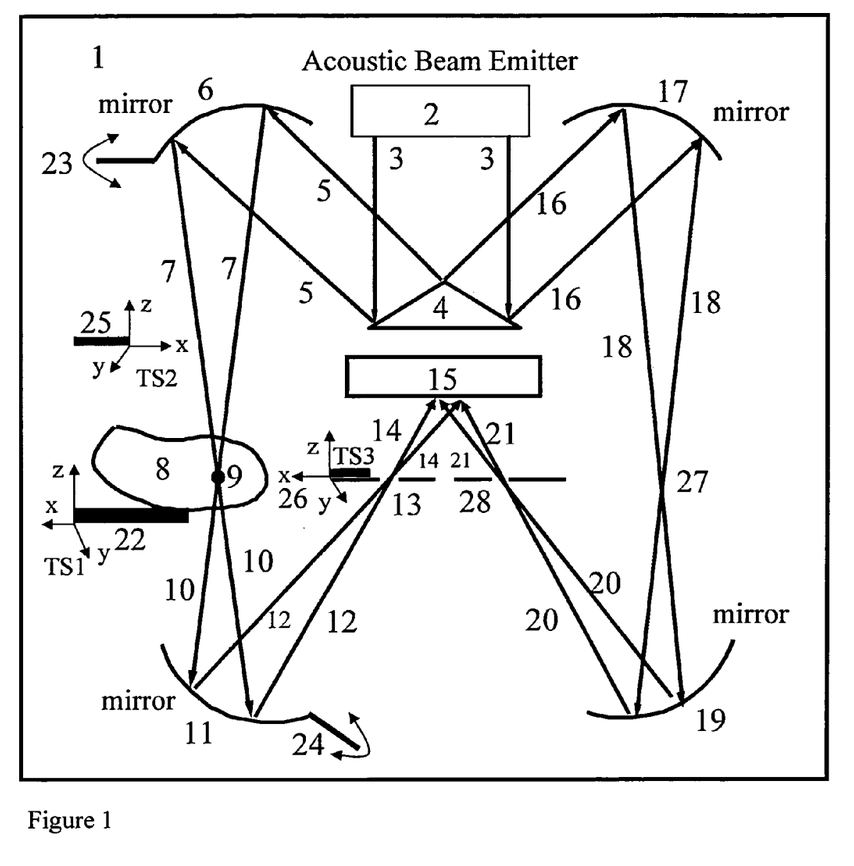
FIG. 1 is a transmission Acoustic Confocal Interferometry microscope in accordance with a first embodiment of the invention.

FIG. 1 shows the illustration of the transmission Acoustic Confocal Interferometry microscope 1 according to a first embodiment of the present invention. The width of the acoustic beam is indicated by two lines numbered the same. A coherent radiation source 2 such as an acoustic actuator emits an acoustic beam 3. Acoustic beam 3 has a large cross sectional area typically on the order of centimeters. Beam 3 passes to biprism 4, where beam 3 is reflected and split into two beams consisting of object beam (first segment) 5 and interference beam (first segment) 16. Object beam (first segment) 5 passes to mirror 6. Mirror 6 reflects and focuses object beam (second segment) 7 towards object 8. Object beam (second segment) 7 converges and crosses over inside object 8 forming probe 9 at the point of cross-over. From probe 9, object beam (third segment) 10 passes out of the object. Object beam (third segment) 10 contains the information of the object 8 and is commonly referred to as the object beam. Object beam (third segment) 10 passes to mirror 11. Mirror 11 reflects and refocuses object beam (fourth segment) 12 towards the object beam pinhole aperture 13. The object beam pinhole aperture 13 allows the focused part of object beam (fifth segment) 14 to pass through a hole of the object beam pinhole aperture 13. The pinhole aperture does not allow the unfocused part of object beam (fifth segment) 14 to pass through, which comprises the aberrated part of the beam from the focusing mirrors 6, 11 and diffusely scattered part of the beam from the object 8. Object beam (fifth segment) 14 then passes to an acoustic detector 15 where the object object beam (fifth segment) 14 interferes with interference beam (fourth segment) 21 (described separately, next paragraph) forming an interferogram. The interferogram is analyzed to determine its amplitude and phase according to techniques known in the art.

For establishing the interference beam, beam 3 passes to biprism 4, where beam 3 is reflected and split into two beams consisting of object beam (first segment) 5 and interference beam (first segment) 16. Interference beam (first segment) 16 passes to mirror 17. Mirror 17 reflects interference beam (first segment) 16 to make interference beam (second segment) 18 that passes to mirror 19. Mirror 19 reflects interference beam (second segment) 18 to make interference beam (third segment) 20. Mirror 19 focuses interference beam (third segment) 20 towards the pinhole aperture 28. The pinhole aperture 28 allows the focused part of interference beam (third segment) 20 to pass through a hole to make interference beam (fourth segment) 21. The pinhole aperture 28 does not allow the unfocused part of interference beam (third segment) 20 to pass through, which comprises the aberrated part of the beam from the focusing mirrors 17, 19. Interference beam (fourth segment) 21 then passes to an acoustic detector 15 where b interference beam (fourth segment) 21 interferes with object beam (fifth segment) 14 (described earlier, previous paragraph) forming an interferogram. The resulting interferogram is analyzed to determine its amplitude and phase according to techniques known in the art.

In order for the entire object 8 to be observed, all of the focused probe 8 positions of the acoustic object beam (second segment) 7 impinging the object 8 should be made confocal with the object beam pinhole aperture 13. Scanning of the object 8 is achieved by either shifting the object 8, shifting the microscope 1 or by rotating the mirror 6, by rotating the mirror 11 and by shifting the object beam object beam pinhole aperture 13 or a combination of any of these three shifting methods. The following beam scanning methods apply to the first embodiment of the invention.

The transmission Acoustic Confocal Interferometry microscope 1 three-dimensionally scans the probe 9 through the object 8 by three methods. They are:

1) by holding the transmission Acoustic Confocal Interferometry microscope 1 stationary while translating the object 8 in x, y, and z directions by means of the first translation stage (TS1) 22.

2) by holding object 8 stationary while translating the transmission Acoustic Confocal Interferometry microscope 1 in x, y, and z directions by means of a translation stage 2 (TS2) 25.

3) by rotating mirror 6 using rotational scanner 23. The change in direction of object beams 7, 10, 12 and 14 by the change in position of probe 9 is compensated by rotating mirror 11 using rotational scanner 24 and shifting the object beam pinhole aperture 13 using translation stage 3 (TS3) 26.

Figure 2:
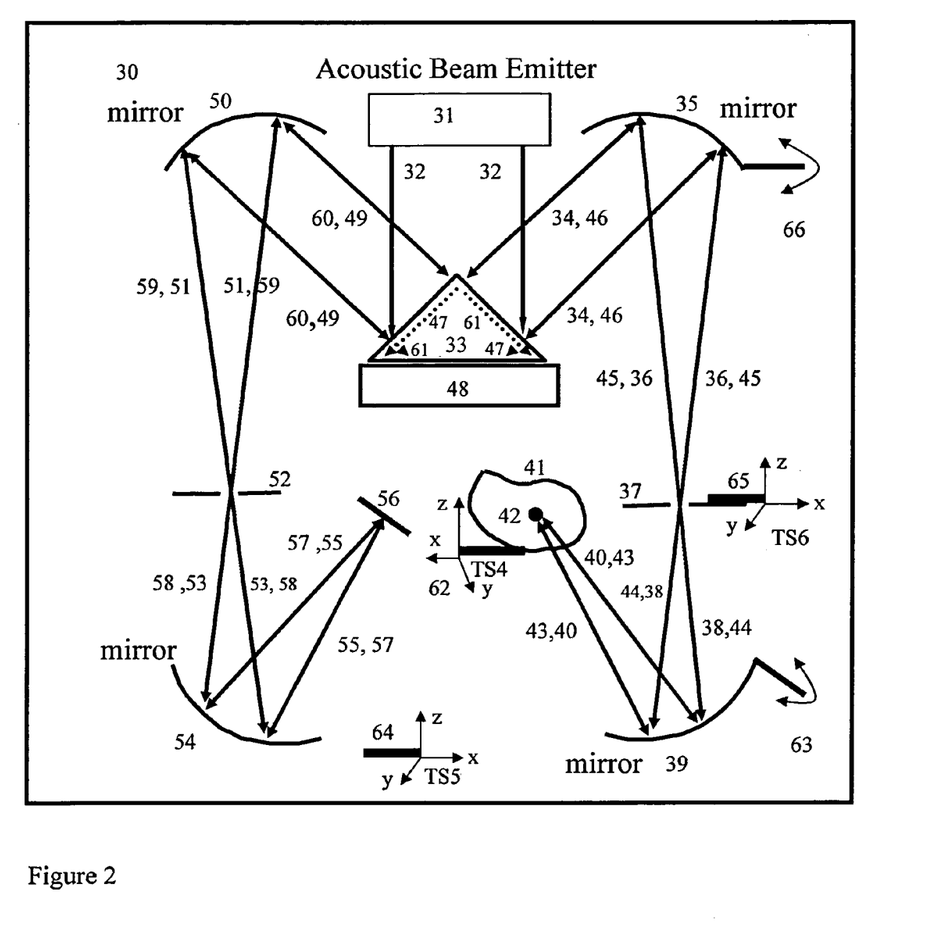
FIG. 2 is a reflection Acoustic Confocal Interferometry microscope in accordance with a second embodiment of the invention.

FIG. 2 shows an illustration of a reflection Acoustic Confocal Interferometry microscope 30 according to a second embodiment of the present invention. The width of the acoustic beam is indicated by two lines each numbered the same. A coherent radiation source 31 such as an acoustic actuator emits an acoustic beam 32. The acoustic beam 32 has a larger cross sectional area typically on the order of centimeters. The beam 32 passes to a semi-transparent biprism 33, where the beam 32 is partially reflected and split into two beams 34 and 49. The semi-transparent biprism 33 is a semi-transparent mirror commonly used in optics where some of the beam is reflected and some of the beam is transmitted, which is a technique known in the art. The beam 34 passes to a mirror 35. The mirror 35 reflects and focuses the beam 36 towards an object beam pinhole aperture 37. The beam 36 converges and passes through the object beam pinhole aperture 37 forming beam 38. The pinhole aperture does not allow the unfocused part of beam 36 to pass through, which comprises the aberrated part of the beam from the focusing mirror 35. The beam 38 passes to a mirror 39. The mirror 39 reflects and refocuses the beam 40 towards the object 41. The beam 40 forms a probe at a focused point 42 inside or on the surface of the object 41. The focused point 42 reflects the beam 43 back towards mirror 39. The beam 43 is the object beam containing the intensity and phase of the object 41 at the focused point 42. The mirror 39 reflects the beam 44 towards the object beam pinhole aperture 37. The object beam pinhole aperture 37 allows only the part of the beam 44 that is confocal or coplanar with the focused probe 42 in the object 41 to pass through the object beam pinhole aperture 37 for the beam 45. The beam 45 then passes to the mirror 35. The mirror 35 reflects the beam 46 towards the biprism 33. The biprism 33 passes some of the intensity of the beam 47 to the detector 48. The detector 48 combines the intensity of the beam 47 with the intensity of the beam 61 forming an interferogram. The resulting interferogram is analyzed to determine the amplitude and phase of the object according to techniques known in the art. The beam 61 is further described in the next paragraph below.

A coherent radiation source 31 such as an acoustic actuator emits an acoustic beam 32. The beam 32 passes to the biprism 33 where the beam 32 is partially reflected and split into two beams 34 and 49. The beam 49 passes to the mirror 50. The mirror 50 reflects and focuses the beam 51 towards a pinhole aperture 52. The beam 51 converges and passes through the pinhole aperture 52 forming beam 53. The beam 53 passes to mirror 54. The mirror 54 reflects and refocuses the beam 55 towards the mirror 56. The mirror 56 reflects the beam 57 directly back towards mirror 54. The mirror 54 then reflects the beam 58 towards the pinhole aperture 52. The pinhole aperture 52 allows only the part of the beam 58 that is confocal or coplanar with the beam 55 that is focused onto the mirror 56 to pass through the pinhole aperture 52 for the beam 59. The beam 59 then passes to the mirror 50. The mirror 50 reflects the beam 60 towards the biprism 33. The biprism 33 passes some of the intensity of the beam 61 to the detector 48. The detector 48 combines the intensity of the beam 61 with the intensity of the beam 47 forming the interferogram. The resulting interferogram is analyzed to determine the amplitude and phase of the object according to techniques known in the art.

Beam Scanning:

In order for the entire object 41 to be observed, all of the focused probe 42 positions of the acoustic beam 40 impinging the object 41 are made confocal with the object beam pinhole aperture 37. Scanning of the object 41 is achieved by either shifting the object 41, shifting the microscope 30 or by rotating the mirror 39, by rotating the mirror 35 and by shifting the object beam PH aperture 37 or a combination of any of these three shifting methods. The following beam scanning methods apply to the second embodiment of the invention.

The reflection Acoustic Confocal Interferometry microscope 30 three-dimensionally scans the probe 42 through the object 41 by three methods. They are:

1) by holding the reflection Acoustic Confocal Interferometry microscope 30 stationary while translating the object 41 in x, y, and z directions by means of the fourth translation stage (TS4) 62.

2) by holding the object 42 stationary while translating the reflection Acoustic Confocal Interferometry microscope 30 in x, y, and z directions by means of translation stage 5 (TS5) 64.

3) by rotating mirror 39 using the rotational scanner 63. Large changes in position of probe 42 are compensated by shifting the object beam pinhole aperture 37 using x, y, z translation stage 6 (TS6) 65 combined with a rotation of mirror 35 using rotational scanner 66.

Figure 3:
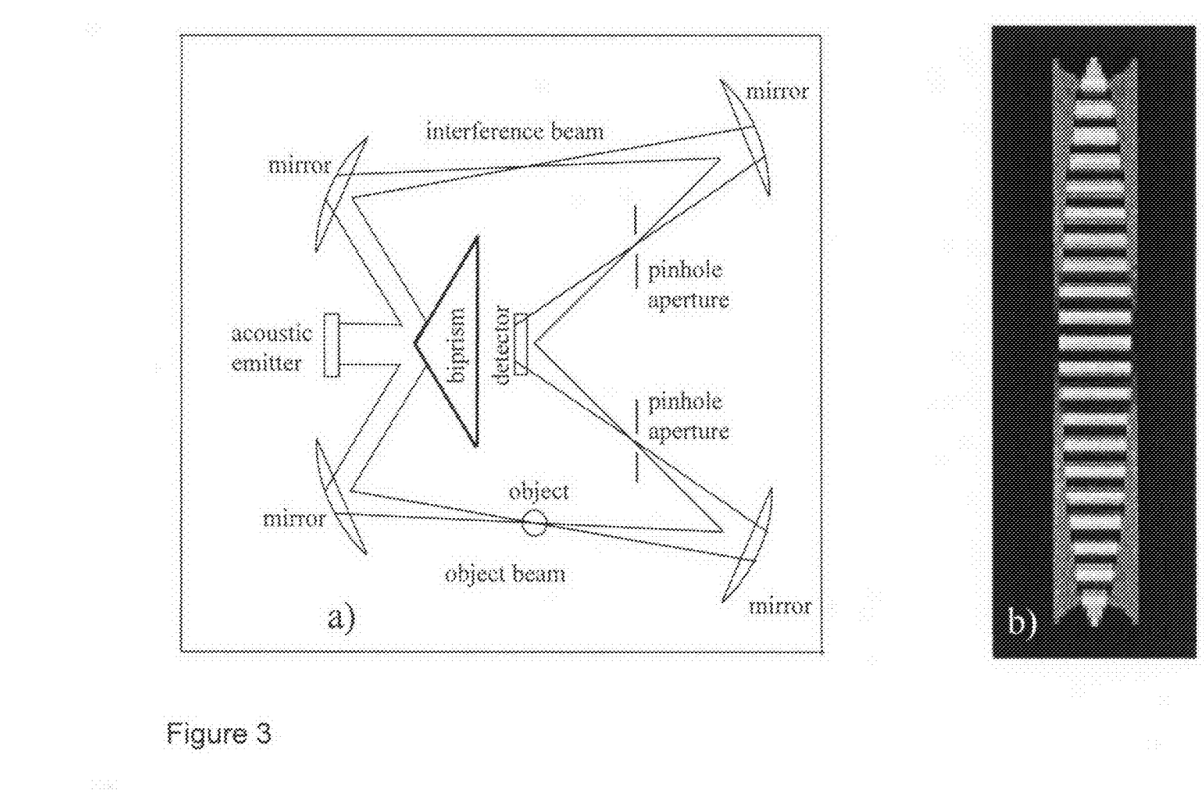
FIG. 3 is a simulation of the transmission Acoustic Confocal Interferometry microscope in accordance with the first embodiment of the invention.
Figure 4:
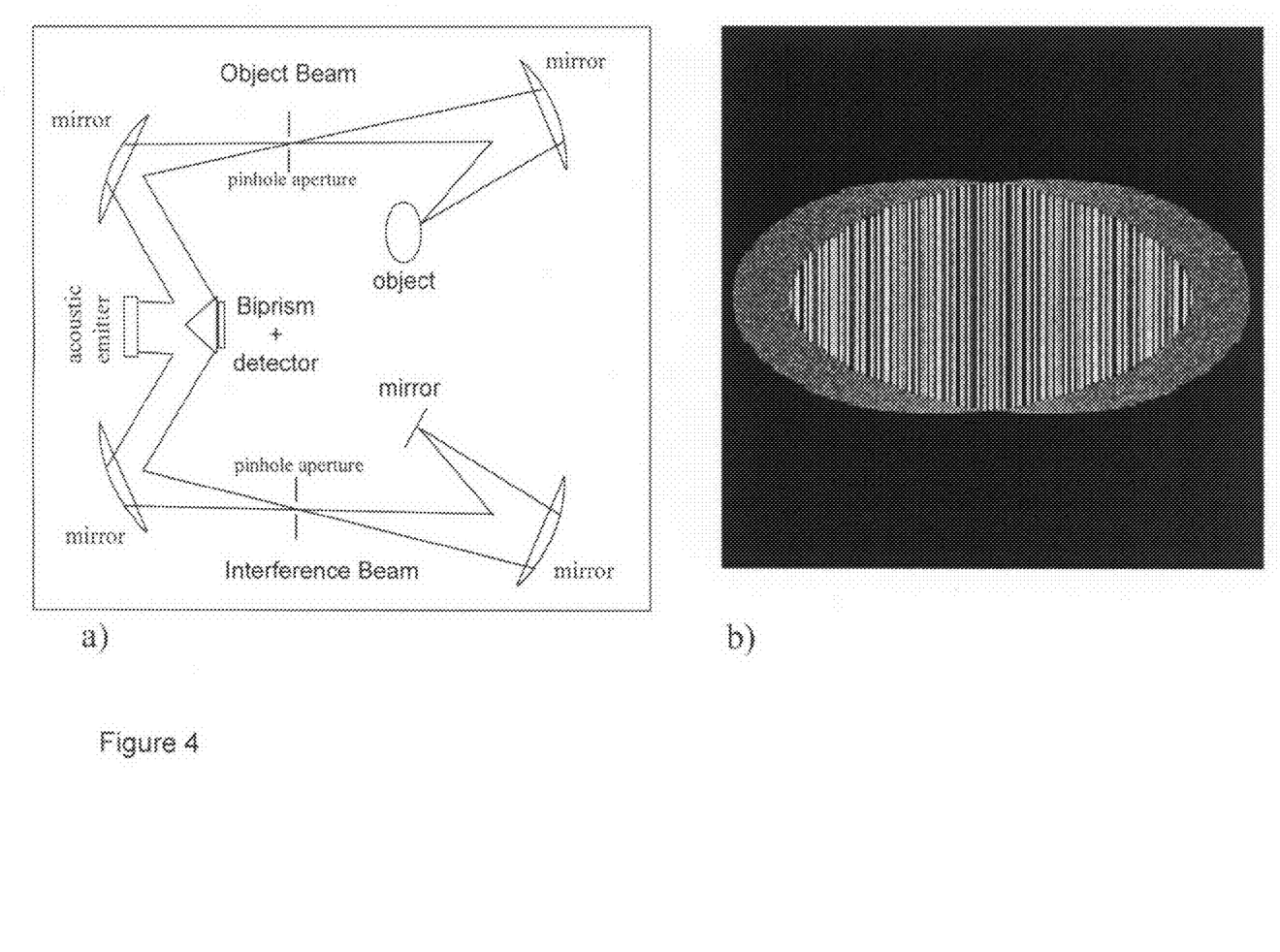
FIG. 4 is a simulation of the reflection Acoustic Confocal Interferometry microscope in accordance with the second embodiment of the invention.

FIG. 3 shows a simulation of the transmission Acoustic Confocal Interferometry microscope in accordance with the first embodiment of the invention. FIG. 4 shows a simulation of the reflection Acoustic Confocal Interferometry microscope in accordance with the second embodiment of the invention.

Figure 5:
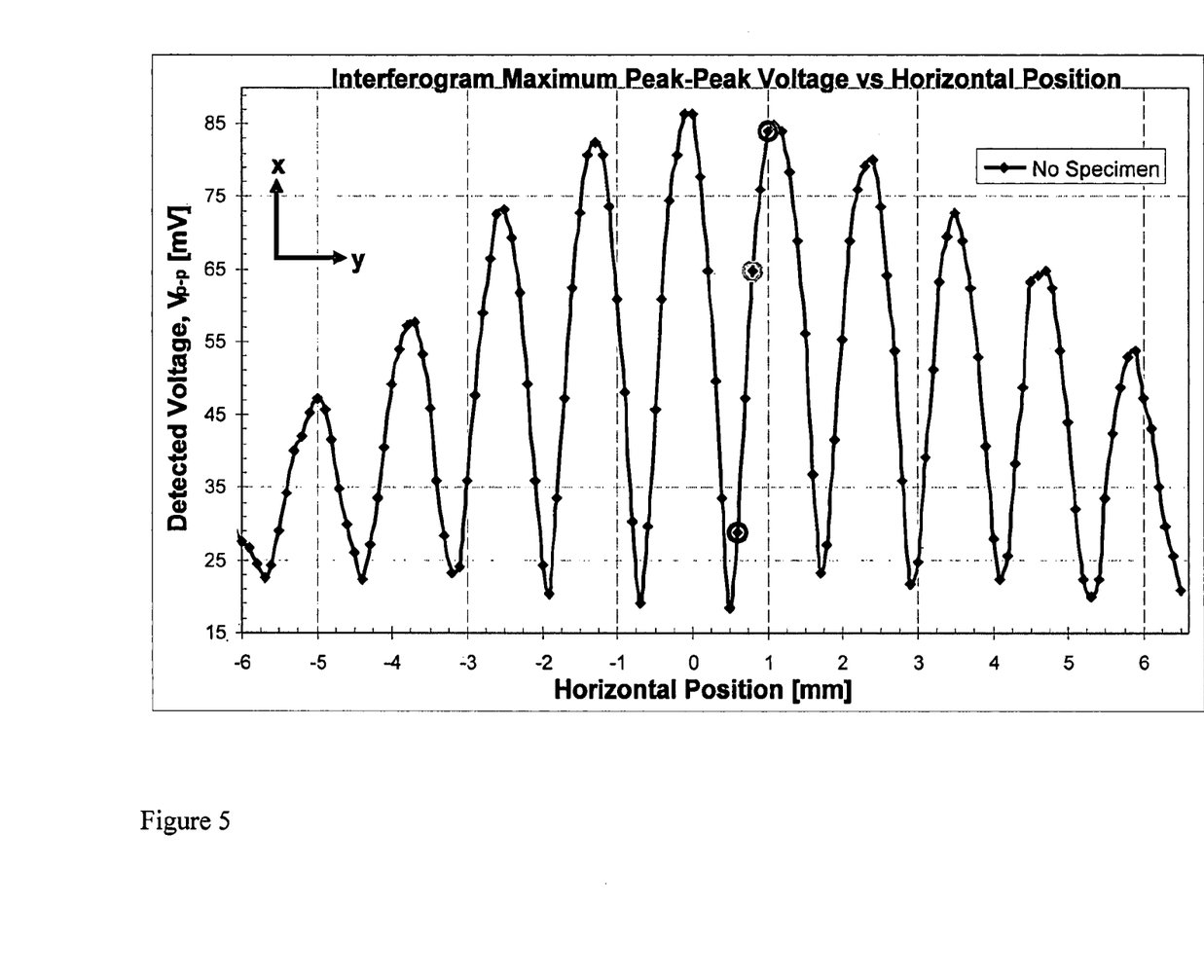
FIG. 5 shows a reference interferogram created by the transmission Acoustic Confocal Interferometry microscope without a specimen in accordance with the first embodiment of the invention.

A reference interferogram without specimen is shown in FIG. 5. The intensity of its fringes can be seen.

Figure 6:
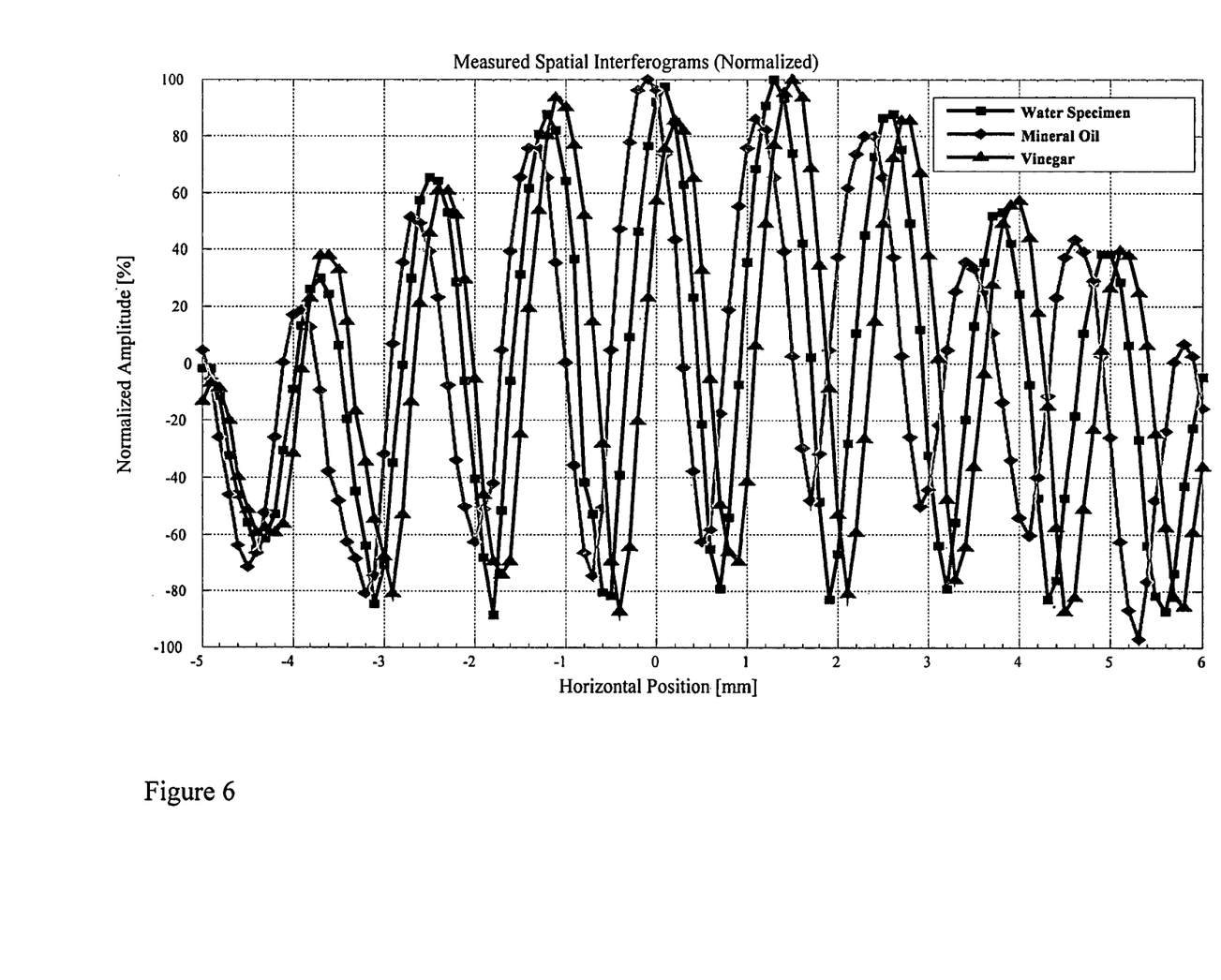
FIG. 6 shows measured interferograms of test specimens consisting of water, mineral oil and vinegar by the transmission Acoustic Confocal Interferometry microscope in accordance with the first embodiment of the invention.

As shown in FIG. 6, which are measured interferograms, a relative phase shift of the fringes due to the difference in speed of sound for 3 different specimens consisting of water, mineral oil and vinegar.

Overall:

Biprism:

In each embodiment the separation between the object beam and the interference beam is controlled by the biprism.

Pinhole Aperture:

In the first embodiment and second embodiment, the pinhole apertures are used to reject any part of the beam that is divergent from the paths of the object beam and the interference beam and to accurately define the beam geometry such as its convergence angle and focal length. The PH apertures allow the object beam and interference beam to form the interferogram on the detector.

Spatial Resolution:

The spatial resolution is set by either the probe size of the beam focused on the object or by the size of the hole of the pinhole aperture, whichever is more restrictive and still enabling sufficient intensity of the beam to pass through the optical system to form the interferogram. The object is always out-of-focus and is only observed in-focus upon combining all of the amplitudes and phases of the points defining the object in proper x, y, z registry.

Example 1

The ACI microscope can be used in medical diagnostics to non-intrusively observe the variations in temperature within the body such as within an organ, muscles, fatty tissue, cancerous tissue and at the interfaces between body organs and their surroundings. Since acoustic waves easily pass through the body, and they can be precisely focused and be made highly coherent, they can be used by the ACI microscope in order to see the body's internal structure, and to measure its state such as composition and temperature. Since the ACI microscope focuses the beam to a probe, which is passed quickly over a point, it can be very gentle on the body by giving a low radiation dose. Once the internal body can be seen by the ACI microscope, by increasing the intensity and dwell time of the beam, treatments to help cure sickness becomes possible, using beam heating methods. Since the ACI microscope can also measure temperature, the temperature of the region of the body being treated by beam heating can be monitored during the treatment process to help ensure a successful treatment.

Example 2

In objects comprising of plasma, gases, liquids, and solids, there are many unanswered questions to simple states of matter, such as the 3D temperature and the 3D composition existing within objects and at interfaces between immiscible and miscible fluids, a container and its contents, and within fluids having various states, such as within a simple flame burning fuel during combustion. The application of the ACI microscope to objects transparent to acoustic beams will answer many of these questions.

Example 3

Because the ACI microscope employs an interferometry method, it measures the "relative" phase information of the object, which is advantageous for measurements of fundamental physical phenomena, and which is also advantageous for performing a high-level, quantitative study. As well, because radiation sources, such as acoustic beams, can now be obtained having very good beam coherence, amplitude and phase images of large objects are possible, on the order of many centimeters. It will be possible with the development of new optical focusing materials to be able to observe much larger objects in the future.

Departures from ACI Microscope:

It will be apparent to one skilled in the art that numerous modifications and departures from the specific embodiments described herein may be made without departing from the spirit and scope of the invention. Variations include different types of beam splitters, different beam rastering systems, different beam directors and different beam focusing devices.

Modifiers such as acoustic fibres, acoustic beam guides and holographic diffusers could also be used. Practical use of the ACI microscope without the pinhole apertures is possible although lower quality object information is obtained. Use of the ACI microscope without the pinhole apertures may have some advantages when the object has low transparency by the beam resulting in low intensity of the object beam at the detector where the beam intensity may be increased sufficiently for collecting information of the object by removal of the pinhole aperture.

The invention claimed is:

1. An Acoustic Confocal Interferometry microscope for use with a suitably selected coherent acoustic or ultrasound source, for the production of an acoustic or ultrasound coherent beam, and a suitably selected detector for providing three dimensional information on an object, said microscope comprising:
   an acoustic or ultrasound coherent wavelength source for producing an acoustic or ultrasound coherent beam;
   scanning means for moving said coherent beam in a suitably selected pattern;
   means for producing an object beam and an interference beam from said acoustic or ultrasound coherent beam;
   object beam focusing means for focusing the object beam to an object focal point;
   an inference beam focusing means for focusing the interference beam to an interference beam focal point, wherein the interference beam focusing means is other than the object focusing means;
   the object beam focusing means and the interference beam focusing means configured to produce a suitably selected convergence angle at a suitably selected position said object beam having a transmission path of essentially the same length of a transmission path of said interference beam, said object beam intercepting an object at the object focal point and said interference beam passing by the object;
   means for defining the object beam and the interference beam based on the geometry of said convergence angle and said position of said object focal point and said interference focal point; and
   means for producing an interference pattern between said object focal point and said interference focal point in order to collect information about the object by a detector.

2. The microscope of claim 1 wherein said means for producing said object beam and said interference beam is a splitting means.

3. The microscope of claim 2 wherein said splitting means is a biprism.

4. The microscope of claim 3 wherein said object beam focusing means is comprised of two object beam mirrors and said interference beam focusing means is comprised of two interference beam mirrors.

5. The microscope of claim 4 wherein said means for scanning said object beam and said interference beam through the object is comprised of one or more of:
   means to shift said object;
   means to shift said microscope; or
   a combination of means to shift said object beam mirrors and means to shift an object beam pinhole aperture used to define the object beam and the inference beam.

6. The microscope of claim 5 wherein said means to shift said object is a first or a fourth translation stage.

7. The microscope, of claim 6 wherein said means to shift said microscope is a second or a fifth translation stage.

8. The microscope of claim 7 wherein said means to shift each object beam mirror[s] is a rotating scanner[s].

9. The microscope of claim 8 wherein said means to shift said object beam pinhole aperture is a third or a sixth translation stage.

10. The microscope of claim 9 wherein a means for defining the object beam and the interference beam based on the geometry of said convergence angle and said position of said object focal point and said interference focal point is confocal with said first object focal point and said first interference focal point.

11. The microscope of claim 10 wherein said means for defining the object beam and the interference beam based on the geometry of said convergence angle and said position of said object focal point and said interference focal point comprises a dual pinhole aperture for limiting passage of said object and said interference beam therethrough.

12. The microscope of claim 11 wherein said means for producing an interference pattern between said object focal point and said interference focal point comprises a means for collecting said first object focal point and said first interference focal point after said first object focal point and after said first interference focal point and a means for focusing said collected object and interference beams to a second object focal point and a second interference focal point at the dual pinhole aperture[s].

13. The microscope of claim 12 wherein said means to shift said object is the fourth-translation stage.

14. The microscope of claim 13 wherein said means to shift said microscope is the fifth translation stage.

15. The microscope of claim 14 wherein said means to shift said object beam pinhole aperture is the sixth translation stage.

16. A method for providing three dimensional information on an object comprising projecting an acoustic or ultrasound coherent beam from an acoustic or ultrasound coherent wavelength source, splitting the coherent beam into an object beam and an interference beam, independently focusing the resultant two beams using separate optics, ensuring the length of the two beams are essentially equivalent, intercepting the object with said object beam at an object focal point, avoiding the object with the interference beam while having an interference focal point on the same plane as the object focal point, refocusing the two beams to second focal points that are confocal with the object and interference focal points, limiting the beams and forming an interference pattern for detecting.

17. The method of claim 16 further comprises intercepting and reflecting said interference beam at said interference beam focal point, and reflecting said object beam off the object before refocusing said beams.

18. An acoustic confocal interferometry microscope, comprising:
   a scanner configured to receive and scan an acoustic beam;
   an acoustic beam splitter to produce an object beam and an interference beam;
   an object beam shaping system configured to focus the object beam to an object focal point;
   an interference beam shaping system configured to focus the interference beam to an interference focal point, the systems configured to converge the object and interference beams at a selected convergence angle at a selected position,
   wherein the object beam intercepts an object at the object focal point; and an acoustic detection system configured to receive the object beam and the interference beam and produce and interference of the object beam and the interference beam.

* * * * *